United States Patent [19]

Bair

[11] Patent Number: 4,827,034

[45] Date of Patent: May 2, 1989

[54] CARBOCYCLIC DERIVATIVES

[75] Inventor: Kenneth W. Bair, Chapel Hill, N.C.

[73] Assignee: Burroughs Wellcome Co., Research Triangle Park, N.C.

[21] Appl. No.: 146,286

[22] Filed: Jan. 20, 1988

Related U.S. Application Data

[63] Continuation of Ser. No. 801,060, Nov. 22, 1985, abandoned, which is a continuation-in-part of Ser. No. 673,531, Nov. 20, 1984, abandoned.

[51] Int. Cl.$^4$ .................... C07C 93/00; C07C 87/78; C07C 87/64
[52] U.S. Cl. .................. 564/387; 260/501.12; 260/501.18; 260/503; 260/503.5; 562/404
[58] Field of Search .............. 564/387; 260/501.12, 260/501.18, 503, 503.5; 562/404

[56] References Cited

U.S. PATENT DOCUMENTS

| | | | |
|---|---|---|---|
| 4,511,582 | 4/1985 | Bair | 514/654 |
| 4,530,800 | 7/1985 | Bair | 260/501.21 |
| 4,532,344 | 7/1985 | Bair | 560/252 |
| 4,551,282 | 11/1985 | Bair | 260/501.18 |
| 4,719,046 | 1/1988 | Bair | 260/501.18 |
| 4,719,047 | 1/1988 | Bair | 260/501.18 |
| 4,719,048 | 1/1988 | Bair | 260/501.18 |
| 4,719,049 | 1/1988 | Bair | 260/501.18 |
| 4,719,055 | 1/1988 | Bair | 260/501.12 |
| 4,719,236 | 1/1988 | Bair | 514/577 |
| 4,720,587 | 1/1988 | Bair | 564/387 |

FOREIGN PATENT DOCUMENTS

0125702A2  11/1984  European Pat. Off. ............ 514/654

Primary Examiner—Glennon H. Hollrah
Assistant Examiner—Raymond Covington
Attorney, Agent, or Firm—Donald Brown

[57] ABSTRACT

The present invention relates to compounds of formula (I)

$$ArCH_2R^1 \qquad (I)$$

or a monomethyl or monoethyl ether thereof (the compound of formula (I) including these ethers may contain no more than 30 carbon atoms in total); ethers, esters, thereof; acid addition salts thereof; wherein Ar is a $C_{15-18}$ fused tetracarbocyclic ring system containing 3 or 4 aromatic rings or a $C_{17-22}$ fused pentacarbocyclic ring system containing 4, or 5 aromatic rings, or a substituted derivative thereof; the ring system Ar should be planar or deviate only slightly from planarity. Thus, the ring system contains a maximum of two non-aromatic carbon atoms which may be in the same ring, in which case they are adjacent, or in different rings;

Ar is not perylene, fluoranthene, chrysene, pyrene, or triphenylene;

$R^1$ contains not more than eight carbon atoms and is a group

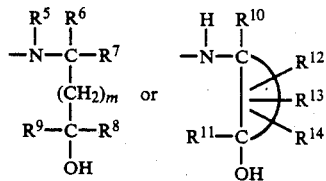

wherein m is 0 or 1;

$R^5$ is hydrogen;

$R^6$ and $R^7$ are the same or different and each is hydrogen or $C_{1-5}$ alkyl optionally substituted by hydroxy;

$R^8$ and $R^9$ are the same or different and each is hydrogen or $C_{1-3}$ alkyl;

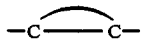

is a five- or six-membered saturated carbocyclic ring;

$R^{10}$ is hydrogen, methyl or hydroxymethyl;

$R^{11}$, $R^{12}$ and $R^{13}$ are the same or different and each is hydrogen or methyl;

$R^{14}$ is hydrogen, methyl, hydroxy, or hydroxymethyl.

7 Claims, No Drawings

CARBOCYCLIC DERIVATIVES

This is a continuation of application Ser. No. 801,060, filed Nov. 22, 1985, now abandoned, which is a continuation-in-part of application Ser. No. 673,531 filed Nov. 20, 1984 now abandoned.

The present invention relates to polycyclic alkanol derivatives which have been found to have biocidal activity. More specifically the invention concerns aminoalkanol derivatives containing a polycarbocyclic ring system, methods for the synthesis thereof, pharmaceutical formulations thereof, novel intermediates therefor, and the use thereof as biocidal agents, particularly antitumor agents.

Accordingly, in a first aspect, the present invention provides a compound of the formula (I)

$$ArCH_2R^1 \quad (I)$$

or a monomethyl or monoethyl ether thereof (the compound of formula (I) including these ethers may contain no more than 30 carbon atoms in total); ethers, esters thereof; acid addition salts thereof; wherein Ar is a $C_{15-18}$ fused tetracarbocyclic ring system containing 3 or 4 aromatic rings or a $C_{17-22}$ fused pentacarbocyclic ring system containing 4 or 5 aromatic rings optionally substituted by one or two substituents (the substituents will contain not more than four carbon atoms in total when when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the ring system is optionally substituted by a group $NR^3R^4$ containing not more than 5 carbon atoms wherein $R^3$ and $R^4$ are the same or different and each is a $C_{1-3}$ alkyl group or $NR^3R^4$ forms a five- or six-membered heterocyclic ring optionally containing one or two additional heteroatoms); the ring system Ar should be planar or deviate only slightly from planarity. Thus, the ring system contains a maximum of two non-aromatic carbon atoms which may be in the same ring, in which case they are adjacent, or in different rings.

Ar is not perylene, fluoranthene, chrysene, pyrene, or triphenylene.

$R^1$ contains not more than eight carbon atoms and is a group

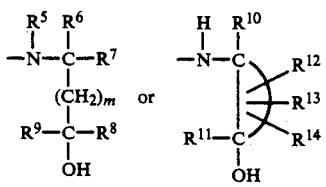

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl;

Suitably $ArCH_2R^1$ or a monomethyl or monoethyl ether thereof contains not more than 28 carbon atoms in total. Suitably, there is a maximum of one non-aromatic carbon in the ring system.

Ar is suitably naphthacenyl, benz[a]anthracenyl, benzo[a]pyrenyl, aceanthrylenyl, aceanthrenyl, 7H-benzo[c]fluoroanthenyl, 11H-benzo[a]fluoranthenyl, acephenanthrylenyl, 4,5-dihydroacephenanthrylenyl, benzo[c]phenanthrenyl, 4H-cyclopenta[def]phenanthrenyl or 11H-benzo[b]fluorenyl (the ring names and numbering systems are shown below),

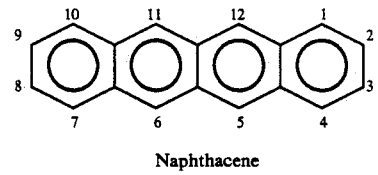

Naphthacene

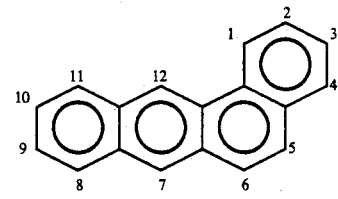

Bezn[a]anthracene

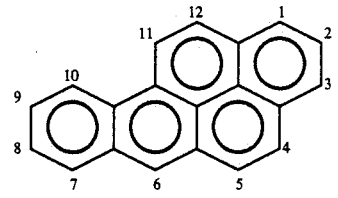

Benzo[a]pyrene

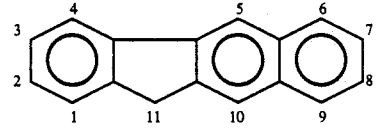

11H—Benzo[b]fluorene

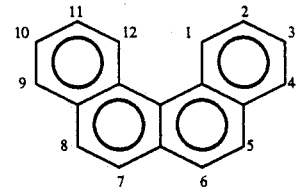

Benzo[c]phenanthrene

-continued

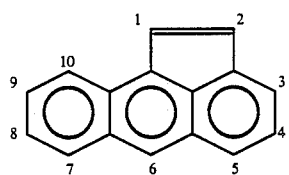

Aceanthrylene

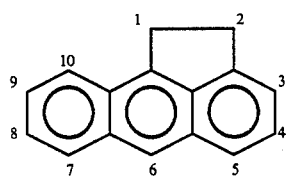

Aceanthrene

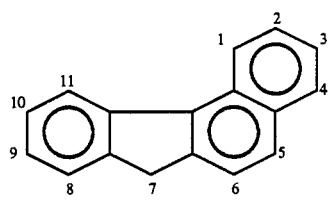

7H—Benzo[c]fluoranthene

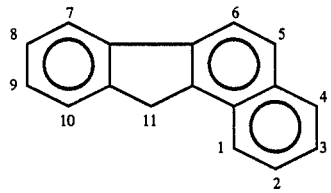

11H—Benzo[a]fluoranthene

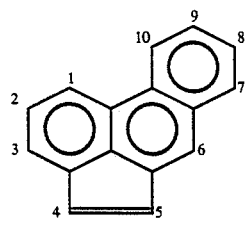

Acephenanthrylene

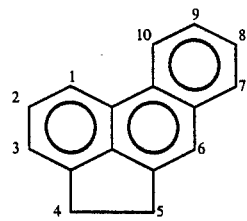

4,5-Dihydroacephenanthrene

-continued

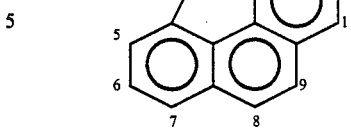

4H—Cyclopenta[def]phenanthrene suitably $R^1$ is

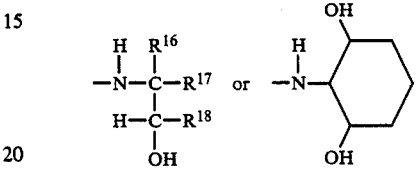

wherein
$R^{16}$ is $CH_2OH$, $CH(CH_3)OH$ or $CH_2CH_2OH$,
$R^{17}$ is hydrogen, $C_{1-3}$ alkyl or $CH_2OH$,
$R^{18}$ is hydrogen or methyl.

Preferably Ar is naphthacenyl, benz[a]anthracenyl, 11H-benzo[b]fluorenyl, acephenanthrylenyl or 4,5-dihydroacephenanthrylenyl;

preferably $R^{16}$ is $CH_2OH$ or $CH(CH_3)OH$; $R^{17}$ is hydrogen, methyl, ethyl or $CH_2OH$.

Most preferably Ar is 5-naphthacenyl, benz[a]anthracen-7-yl, 6-acephenanthrylenyl 4,5-dihydro-6-acephenanthrylen-6-yl or 11H-benzo[b]fluoren-5-yl;

most preferably $R^1$ is a diol of the structure

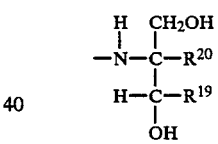

wherein $R^{19}$ is hydrogen or methyl and $R^{20}$ is hydrogen, methyl or ethyl, preferably methyl.

Acid addition salts included within the scope of the present invention are those of compound of formula (I) and ethers and esters thereof.

Esters and nonpharmaceutically useful acid addition salts of the compounds of the formula (I) are useful intermediates in the preparation and purification of compounds of the formula (I) and pharmaceutically useful acid addition salts thereof, and are therefore within the scope of the present invention. Thus, acid addition salts of the compounds of the formula (I) useful in the present invention include but are not limited to those derived from inorganic acids, such as hydrochloric, hydrobromic, sulfuric and phosphoric acids, organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, napthalene-2-sulfonic, and ascorbic acids, as amino acids such as glycine.

Acid addition salts particularly useful as biocidal agents are those that are pharmacologically and pharmaceutically acceptable. Thus, suitable acid addition salts include but are not limited to those derived from hydrochloric, methanesulfonic, ethanesulfonic, isethionic, lactic, and citric acids.

The preferred pharmacologically and pharmaceutically acceptable acid addition salts are those that are soluble in solvents suitable for parenteral administration, for example, hydrochlorides, methanesulfonates and isethionates.

Esters of compounds of formula (I) are derived from acids known to those skilled in the art to be suitable for ester formation, and are conveniently those derived from $C_{1-6}$ alkanoic acids or alkanoic acid derivatives, for example acetic acid, propionic acid, n-butyric acid and iso-butyric acid. The esters may be formed from all or only some of the hydroxy groups contained in the compounds of formula (I). Specific compounds within the scope of formula (I) include;

2-[(Benz[a]anthraceny-7-lmethyl)amino]-2-methyl-1,3-propanediol,
2-[(Benzo[a]pyren-6-ylmethyl)amino]-2-methyl-1,3-propanediol,
2-[(5-Naphthacenylmethyl)amino]-2-methyl-1,3-propanediol,
2-[(11H-Benzo[b]fluoren-5-ylmethyl)amino]-2-methyl-1,3-propanediol,
2-[[(12-Chloro-5-naphthacenyl)methyl]amino]-2-methyl-1,3-propanediol,
2-[(6-Acephenanthrylenylmethyl)amino]-2-methyl-1,3-propanediol
2-[[(4,5-Dihydro-6-acephenanthrenyl)methyl]amino]-2-methyl-1,3-propanediol
2-[(Benz[a]anthracen-3-ylmethyl)amino]-2-methyl-1,3-propanediol
2-[(4H-Cyclopenta[def]phenanthren-1-ylmethyl)amino]-2-methyl-1,3-propanediol
2-[(Benzo[c]phenanthren-5-ylmethyl)amino]-2-methyl-1,3-propanediol;
ethers, esters thereof; acid addition salts thereof.

Of these specific examples of compounds of formula (I), the preferred compounds are
2-[(Benz[a]anthracen-7-ylmethyl)amino]-2-methyl-1,3-propanediol and
2-[(11H-Benzo[b]fluoren-5-ylmethyl)amino]-2-methyl-1,3-propanediol,
2-[(6-Acephenanthrylenylmethyl)amino]-2-methyl-1,3-propanediol,
2-[[(4,5-Dihydro-6-acephenanthrylenyl)methyl]amino]-2-methyl-1,3-propanediol; ethers, esters thereof; acid addition salts thereof.

The compounds of formula (I) and their ethers, esters and acid addition salts thereof may be prepared by any method known in the art for the preparation of compounds of analogous structure. Thus, the compounds of formula (I) may, for example, be prepared by any of the methods defined below.

1. The reduction of a compound of formula (II)

Wherein $R^2$–$R^4$ and $R^6$–$R^{14}$ and m are as hereinbefore defined or a suitably protected derivative thereof followed by deprotection where appropriate.

The conditions and reagents for such a reaction are well known to those skilled in the art, and any such conditions/reagents may be employed. The conversion of (II) or suitably protected derivatives thereof may be carried out by a reducing agent followed by deprotection if necessary. The reduction is conveniently carried out by a metal hydride such as lithium aluminum hydride, sodium borohydride, sodium cyanoborohydride, or by catalytic hydrogenation, conveniently by hydrogen in the presence of a metal catalyst such as palladium or platinum, or equivalent reagents as outlined by J. March, *Advanced Organic Chemistry*, 2nd ed., pages 819–820, McGraw Hill, New York, 1977. The reduction is suitably carried out with the compound of formula (II) in solution in an inert solvent or mixture of solvents compatible with the reducing agent, at a non-extreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethyl ether or tetrahydrofuran).

In the case of sodium cyanoborohydride and like reagents, suitable solvents include those described for sodium borohydride and in the presence of an acid conveniently glacial acetic acid or ethanolic hydrochloric acid as outlined in, for example, R. Hutchins et al., *Organic Preparations and Procedures International* 11, 201 (1979).

In the case of catalytic hydrogenation, suitable solvents include alcohols (for example methanol and ethanol) optionally in the presence of a hydrocarbon cosolvent (for example toluene or benzene) or other cosolvent (for example diethyl ether or tetrahydrofuran) in the presence of an acid (for example glacial acetic acid or ethanolic hydrochloric acid) or in glacial acetic acid.

Protected derivatives of compounds of formula (II) are conveniently used when lithium aluminum hydride is employed as a reducing agent. Convenient protecting groups are compatible with the reducing agent utilizing and are readily removed under nondestructive conditions, for example benzyl, tetrahydropyranyl and isopropylidene ethers.

It is often convenient not to isolate the compound of the formula (II) but to react a compound of the formula (III) with a compound of the formula (IV):

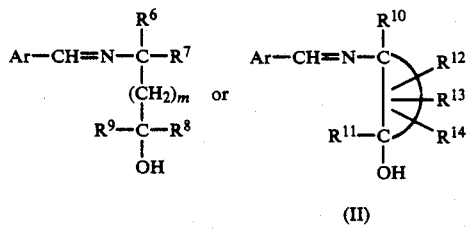

(II)

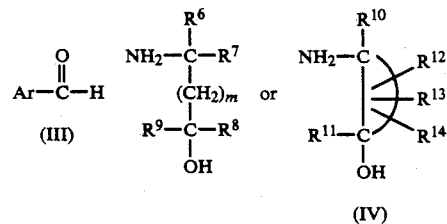

(IV)

wherein Ar and $R^2$-$R^4$ and $R^6$-$R^{14}$ and m are as defined in (I), and reduce the compound of the formula (II) so formed in situ. The reaction of the compounds of the formulae (III) and (IV) is again suitably carried out using conditions and reagents which are well known to those skilled in the art, for example in the presence of an acid, such as a sulfonic acid, i.e., p-toluenesulfonic acid, in an appropriate inert solvent, such as an aromatic hydrocarbon, suitably toluene, with azeotropic removal of water followed by treatment with the reducing agent in an appropriate solvent, suitably ethanol or methanol. Alternatively, (II) formed under equilibrium conditions in appropriate solvents can be reduced in situ with an appropriate reducing agent, suitably sodium cyanoborohydride. The compound of formula (III) may be in the form of a protected aldehyde, for example an acetal, which liberates the aldehyde function under the reaction conditions.

In turn, a compound of formula (III) can be synthesized by reacting the appropriate polycarbocyclic ring system with a formylating agent such as that generated by the reaction between $SnCl_4$ and $Cl_2CHOCH_3$ or equivalent reagents, for example, according to the method of A. Rieche et al., Chem. Ber. 93, 88 (1960), or with other standard formylating reagents/procedures known to the art, for example, the Gatterman-Koch ($CO/HCl/AlCl_3/CuCl$), the Gatterman reaction ($HCN/HCl/ZnCl_2$), and the Vilsmeier reaction ($POCl_3/PhN(Me)CHO$, or $POCl_3/Me_2NCHO$) (J. March, vide supra, pages 494–497).

The compounds of the formula (III) may also be prepared from an appropriate polycarbocyclic ring system substituted by a suitable functional group such as (but not limited to) esters, $CH_2OH$, $CHBr_2$, $CH_3$, $COCH_3$, $COOH$, or $CN$, and converting this functional group to an aldehyde group by methods well known to those skilled in the art.

Where the polycarbocyclic ring system bears substituents, the compound of formula (III) may be prepared by a variety of methods known in the art of organic chemistry depending on the nature of the substituent on the polycyclic ring. For example, if the substituent(s) is a halogen, the starting materials may be prepared by direct treatment of the appropriate polycarbocyclic ring system with a halogenating agent (e.g., $Cl_2$, $Br_2$, or $SO_2Cl_2$) or indirectly by such routes as the Sandmeyer reaction (H. H. Hodgson, Chem. Rev. 40, 251 (1947). If the substituent(s) is alkyl, the polycarbocyclic ring system may be reacted with the appropriate reagents under Friedel-Crafts reaction conditions (G. A. Olah, Friedel Crafts and Related Reactions, Vols. 1–3, Interscience, New York, NY, 1963-1965).

In appropriate cases, the compounds of the formula (IV) and ethers thereof also may be prepared by methods known in the art, for example, by the reaction of a compound of the formula (V)

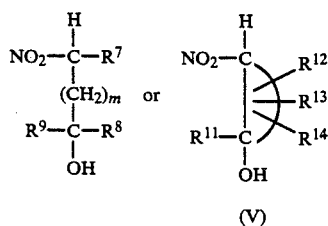

(V)

(or ethers thereof) where $R^{7-9}$ and $R^{11}$-$R^{14}$ and m are as hereinbefore defined with an appropriate aldehyde, conveniently acetaldehyde or formaldehyde (as in B. M. Vanderbilt and H. B. Hass, Ind. Eng. Chem. 32, 34 (1940)) followed by reduction (as outlined in J. March, vide supra, pages 1125–1126), conveniently by hydrogen and a metal catalyst (for example, a platinum containing catalyst) in an appropriate solvent, conveniently glacial acetic acid.

2. The reduction of a compound of the formula (VI)

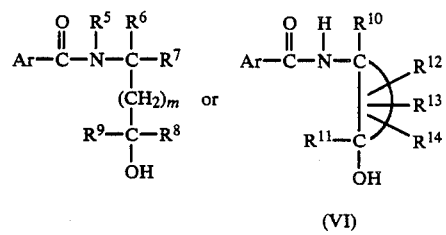

(VI)

wherein Ar and $R^2$-$R^{14}$ and m are as hereinbefore defined and the hydroxy groups are optionally protected, followed by deprotection of the hydroxy groups where appropriate. The reduction may be carried out by standard reducing agents known for carrying out this type of reduction (as outline in J. March, vide supra, page 1122), for example, a hydride reagent such as lithium aluminium hydride in an inert solvent, such as an ether, i.e., tetrahydrofuran, at a non-extreme temperature, for example, at between 0° and 100° C. and conveniently at the reflux temperature of the ether. The compound of the formula (VI) may be formed by the reaction of the appropriate acid (ArCOOH) or a suitable reactive acid derivative thereof (as outlined in J. March, vide supra, pages 382–390), for example, an acid halide, in an inert solvent with an amine of the formula (IV) in which the hydroxy groups are optionally protected, for example, when the compound of the formula (IV) is a diol, by an isopropylidene group. The compound of the formula (IV) so formed is suitably reduced in situ and deprotected if necessary to give a compound of formula (I). The compounds of the formula ArCOOH can be prepared by methods well known to those skilled in the art.

3. The reaction of a compound $ArCH_2L$ (wherein Ar is as hereinbefore defined and L is a leaving group) with a compound of the formula (IV) as hereinbefore defined. Suitable leaving groups are those defined by J. March, vide supra, pages 325–331, and include halogens such as chlorine and bromine and sulfonic acid derivatives such as p-toluenesulfonate. The reaction is suitably carried out in an appropriate solvent, such as a dipolar aprotic solvent or alcohol at a non-extreme temperature, for example 50°–100°. The compounds of the formula $ArCH_2L$ can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have biocidal activity, e.g., are toxic to certain living cells which are detrimental to mammals, for example pathogenic organisms and tumor cells. While the compounds herein have biocidal activity, it should be appreciated that the range and level of activity may vary from compound to compound, and therefore the compounds are not necessarily equivalent.

This toxicity to pathogenic organisms has been demonstrated by activity against viruses (e.g., *Herpes simplex* 1/vero), fungi (e.g., *Candida albicans*), protozoa (e.g., *Eimeria tenella* and *Trichomonas vaginalis*), bacteria (e.g., *Mycoplasma smegmatis* and *Streptococcus pyogenes*), and helminths (e.g., *Nippostrongylus brasiliensis*). The antitumor activity of compounds of formula (I) has been demonstrated in a number of recognized screens and primarily by activity against ascitic P388/0 leukemia.

Preferred compounds of the formula (I) are those which have antitumor activity. The activity against ascitic tumors, including P388/0, is evidenced by reduction of tumor cell number in mammals (for example, mice bearing ascitic tumors) and consequent increase in survival duration as compared to an untreated tumor-bearing control group. Antitumor activity is further evidenced by measurable reduction in the size of solid tumors following treatment of mammals with the compounds of this invention compared to the tumors of untreated control tumor-bearing animals. Compounds of formula (I) are active against murine tumors such as lymphocytic leukemia P388/0, lymphocytic leukemia L1210, melanotic melanoma B16, P815 mastocytoma, MDAY/D2 fibrosarcoma, colon 38 adenocarcinoma, M5076 rhabdomyosarcoma and Lewis lung carcinoma.

Activity in one or more of these tumor tests has been reported to be indicative of antitumor activity in man (A. Goldin et al., in *Methods in Cancer Research* ed. V. T. DeVita Jr. and H. Busch, 16 165, Academic Press, N.Y. 1979).

There are sublines of P388/0 which have been made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388/0 above.

Compounds of formula (I) have also been found to be active against human tumor cells in primary cultures of lung, ovary, breast, renal, melanoma, unknown primary, gastric, pancreatic, mesothelioma, myeloma, and colon cancer. As used herein "cancer" is to be taken as synonymous with "malignant tumor" or more generally "tumor" unless otherwise noted. This is a procedure in which the prevention of tumor cell colony formation, i.e., tumor cell replication, by a drug has been shown to correlate with clinical antitumor activity in man (D. D. Von Hoff et al., *Cancer Chemotherapy and Pharmacology* 6, 265 (1980); S. Salmon and D. D. Von Hoff, *Seminars in Oncology*, 8, 377 (1981)).

Compounds of formula I which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, New York, 1979, lying in the range between −2.0 and +2.5.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumor agent.

The amount of compound of formula (I) required to be effective as a biocidal agent will, of course, vary and is ultimately at the discretion of the medical or veterinary practitioner. The factors to be considered include the condition being treated, the route of administration, the nature of the formulation, the mammal's body weight, surface area, age and general condition, and the particular compound to be administered. A suitable effective antitumor dose is in the range of about 0.1 to about 120 mg/kg body weight, preferably in the range of about 1.5 to 50 mg/kg, for example 10 to 30 mg/kg. The total daily dose may be given as a single dose, multiple doses, e.g., two to six times per day, or by intravenous infusion for a selected duration. For example, for a 75 kg mammal, the dose range would be about 8 to 9000 mg per day, and a typical dose would be about 2000 mg per day. If discrete multiple doses are indicated, treatment might typically be 500 mg of a compound of formula I given 4 times per day in a pharmaceutically useful formulation.

While it is possible for the active compound (defined herein as compound of formula (I), or ether, ester, or salt thereof) to be administered alone, it is preferred to present the active compound in a pharmaceutical formulation. Formulations of the present invention, for medical use, comprise an active compound together with one or more pharmaceutically acceptable carriers thereof and optionally other therapeutical ingredients. The carrier(s) must be pharmaceutically acceptable in the sense of being compatible with the other ingredients of the formulation and not deleterious to the recipient thereof.

The present invention, therefore, further provides a pharmaceutical formulation comprising a compound of formula (I) (in the form of the free base, ether, or ester derivative or a pharmaceutically acceptable acid addition salt thereof) together with a pharmaceutically acceptable carrier therefor.

There is also provided a method for the preparation of a pharmaceutical formulation comprising bringing into association a compound of formula (I), an ether, ester, or pharmaceutically acceptable salt thereof, and a pharmaceutically acceptable carrier therefor.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter.

Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

General Comments

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatography" $SiO_2$ (Merck & Co., Inc., Merck Chemical Division, Rahway, NJ, 07065, Silica Gel 60, 230–400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR and MS data of all new products were consistent with the expected and proposed structures. The positions assigned to structural isomers were unequivocally determined by a number of NMR techniques. All final products were dried in a vacuum oven at 20 mm Hg pressure at the temperature indicated overnight (12–16 h). All temperatures are in degrees Celsius. Other abbreviations used are: room temperature (RT), absolute (abs.), round bottom flask (RB flask), minutes (min), hours (h).

Example 1.
2-[(Benz[a]anthracen-7-ylmethyl)amino]-2-methyl-1,3-propanediol methanesulfonate To a 3-necked RB flask equipped with magnetic stirring bar, condenser, thermometer, Dean-Stark trap, and $N_2$ inlet line with bubbler was added benz[a]anthracene-7-carbaldehyde (Cambridge Chemical, Inc., 202 E. Smith St., Milwaukee, WI 53207, 5.13 g, 20 mmol), 2-amino-2-methyl-1,3-propanediol (Aldrich Chemical Co., P.O. Box 2060, Milwaukee, WI 53201, 4.20 g, 40 mmol), p-toluenesulfonic acid monohydrate (Aldrich, 0.1 g), and $PhCH_3$ (250 mL). The mixture was stirred at reflux with removal of $H_2O$ for 3 h (or in the case of other examples until no $H_2O$ is collected). Most of the $PhCH_3$ was then removed by distillation. The mixture was then cooled in an ice bath and diluted with abs. EtOH (200 mL) and further cooled. Solid $NaBH_4$ (MCB Manufacturing Chemists, Inc., 2909 Highland Ave., Cincinnati, OH 45212, 1.51 g, 40 mmol) was added in one portion of the reaction mixture. The ice bath was then removed, the reaction mixture allowed to warm to RT and further stirred overnight. The reaction was then basified with 1N NaOH (2 L). The white solid which formed was filtered, washed with $H_2O$ (4 L), and sucked semidry. The solid was then dissolved in a mixture of abs. EtOH (100 mL) and $CH_3SO_3H$ (99.5%, Morton Thiokol, Inc.—Alfa Products, P.O. Box 299, 152 Andover Street, Danvers, MA 01923, 3 mL), filtered and diluted to 2 L with $Et_2O$. After filtration, two additional crystallizations (EtOH/$Et_2O$) and drying, 7.48 g (84.7%) of 2-[(benz[a]anthracen-7-ylmethyl)amino]-2-methyl-1,3-propanediol methanesulfonate was obtained, mp 233°–234° (dec), (C, H, N, S).

In other analogous procedures the solvent was removed by rotary evaporation before the addition of 1N NaOH or alternatively, H₂O. The crude wet product can also be dried at 100° overnight in a vacuum oven to remove most of the H₂O before salt formation. Additionally, i-PrOH and CH₃OH can be used in combination with Et₂O or hexane as the recrystallization solvent for these salts.

Example 2.
2-[(Benzo[a]pyren-6-ylmethyl)amino]-2-methyl-1,3-propanediol methanesulfonate.0.25H₂O Using the reductive amination procedure outlined in Example 1, benzo[a]pyrene-6-carbaldehyde (Cambridge Chemical, Inc.) and 2-amino-2-methyl-1,3-propanediol (Aldrich) gave 2-[(benzo[a]pyren-6-ylmethyl)amino]-2-methyl-1,3-propanediol methansulfonate.0.25H₂O in 53.1% yield, mp darkens >195°, 275° (dec), (C, H, N, S).

Example 3.
2-[(5-Naphthacenylmethyl)amino]-2-methyl-1,3-propanediol

3A. Naphthacene-5-carbaldehyde and
3B. Naphthacene-5,11-dicarbaldehyde To a 3-necked RB flask equipped with overhead mechanical stirrer, condenser, addition funnel, N₂ inlet line with bubbler was added N-methylformanilide (Aldrich, 89.21 g, 0.66 mol, 81 mL) and o-dichlorobenzene (Aldrich, 200 mL). The mixture was cooled to 10° with an ice bath. Phosphorus oxychloride (Aldrich, 101.21 g, 0.66 mol, 60 mL) was then added dropwise to the solution not allowing the reaction temperature to rise above 10°. The reaction mixture was then allowed to warm to RT. Solid naphthacene (Cambridge Chemical, Inc., 50 g, 0.22 mol) was then added in five portions over 5 min. The reaction mixture was warmed slowly to 80° (the mixture turns from purple to an almost black color). The reaction was stirred at 80° for 12 h, cooled, poured into ice water (2 L) and stirred an additional 12 h at RT. The mixture was then filtered. The organic layer in the filtrate was dried (Na₂SO₄) and applied to a plug of SiO₂ (500 g) and eluted first with PhCH₃ followed by CH₂Cl₂. The appropriate fractions were combined and the solvent removed by rotary evaporation. Recrystallization (CH₂Cl₂/EtOAc) gave 17.5 g (31.1% yield) of naphthacene-5-carbaldehyde, mp 163°-164° (Lit. 164°, N. P. Buu-Hoi et al., Recueil 76 674 (1975)), (C, H). The solid from the filtration of the crude reaction mixture was washed with a large volume of CH₃OH (5×200 mL), dissolved in THF (4 L) and passed through a plug of SiO₂ (500 g) using an additional 2 L of THF as eluting solvent. The solvent was reduced to a volume of 300 mL and then diluted to 800 mL with EtOAc. The solvent volume was reduced to 250 mL. After filtration and drying 10.90 g (17.4% yield) of naphthacene-5,11-dicarbaldehyde, mp 247°-250°, (C, H).

3C.
2[(5-Naphthacenylmethyl)amino]-2-methyl-1,3-propanediol methanesulfonate Using the reductive amination procedure described in Example 1, naphthacene-5-carbaldehyde (3A) and 2-amino-2-methyl-1,3-propanediol (Aldrich) gave 50.1% yield of 2-[(5-naphthacenylmethyl)amino]-2-methyl-1,3-propanediol methanesulfonate, mp 197.5°-199°, (EtOH/Et₂O), (C, H, N, S).

Example 4.
2-[(11H-Benzo[b]fluoren-5-ylmethyl)amino]-2-methyl-1,3-propanediol

4A. 11H-Benzo[b]fluorene-5-carbaldehyde

11H-Benzo[b]fluorene (Cambridge Chemical, Inc.) was formylated using the procedure of A. Rieche et al., Chem. Ber. 93, 88 (1980). The crude aldehyde appeared to be mainly one isomer by TLC. The crude material was passed through a plug of SiO₂ using PhCH₃ as the eluting solvent. Removal of the solvent and crystallization (CH₂Cl₂/hexane) gave an 86% yield of 11H-benzo[b]fluorene-5-carbaldehyde, mp 104.5°-106.5°, (C, H).

4B.
2-[(11H-Benzo[b]fluoren-5-ylmethyl)amino]-2-methyl-1,3-propanediol methansulfonate Using the reductive amination procedure outlined in 1, 11H-benzo[b]fluorene-5-carbaldehyde (4A) and 2-amino-2-methyl-1,3-propanediol (Aldrich) gave a 49.6% yield of 2-[(11H-benzo[b]fluoren-5-ylmethyl)amino]-2-methyl-1,3-propanediol methanesulfonate, mp 211°-213°, (C, H, N, S).

Example 5.
2-[(Benzo[c]phenanthren-5-ylmethyl)amino]-2-methyl-1,3-propanediol

5A. Benzo[c]phenanthrene-5-carbaldehyde

Benzo[c]phenanthrene (Cambridge Chemical, Inc.) was formulated using the procedure of A. Rieche et al., Chem. Ber. 93, 88 (1980). The crude aldehyde appeared to be mainly one isomer by TLC. The crude material was purified on a plug of SiO₂ using PhCH₃ as the eluting solvent followed by recrystallization (CH₂Cl₂/hexane) and gave pure material (74% yield) isomerically pure by NMR shown to be benzo[c]phenanthrene-5-carbaldehyde, mp 133°-134°, (C, H).

5B.
2-[(Benzo[c]phenanthren-5-ylmethyl)amino]-2-methyl-1,3-propanediol methanesulfonate Using the reductive amination procedure described in Example 1, benzo[c]phenanthrene-5-carbaldehyde (5A) and 2-amino-2-methyl-propanediol (Aldrich) gave 57.5% of 2-[(benzo[c]phenanthren-5-ylmethyl)amino]-2-methyl-1,3-propanediol methanesulfonate, mp 205°-207° (dec), (EtOH/Et₂O), (C, H, N, S).

Example 6.
2-[[(12-Chloro-5-naphthacenyl)methyl]amino]-2-methyl-1,3-propanediol

6A. 12-Chloronaphthacene-5-carbaldehyde

To a 3-necked RB flask equipped with overhead stirrer, condenser, addition funnel, and N₂ inlet line with bubbler was added 2,3-benz-9-anthrone (prepared by the procedure of L. F. Fieser et al., J. Amer. Chem. Soc. 53, 2329 (1931), 57.3 g, 0.235 mol) and DMF (Aldrich, 400 mL). The mixture was cooled to 0°. Phosphorus oxychloride (MCB, 167.5 g, 1.09 mol, 100 mL) was then added dropwise to the flask while reaction temperature was maintained between 0°-10° over a period of 1.5 h. The reaction color deepened to a dark purple as the reaction temperature was slowly raised to 85°. The reaction was stirred at this temperature for 2 h, cooled and then stirred at RT overnight. The reaction mixture was poured into 2 L of 2.8M NaOAc, vigorously stirred for 30 min, then filtered. The dark purple solid was washed with H₂O (1 L) then with CH₃OH (3×500 mL). After drying in a vacuum (40°) overnight 63.9 g (97.6%) of 12-chloronaphthacene-5-carbaldehyde was obtained which was used without further purification. An analytical sample was recrystallized from CH₂Cl₂/CH₃OH; mp 211.5°–213.5°, (C, H).

6B.
2-[[(12-Chloro-5-naphthacenyl)methyl]amino]-2-methyl-1,3-propanediol methanesulfonate Using the reductive amination procedure outlined in Example 1, 12-chloronaphthacene-5-carbaldehyde (6A) and 2-amino-2-methyl-1,3-propanediol (Aldrich) gave 31.8% yield of 2-[[(12-chloro-5-naphthacenyl)methyl]amino]-2-methyl-1,3-propanediol methanesulfonate, mp 219°–220° (dec), (CH₃OH/Et₂O), (C, H, N, Cl, S).

6C.
2-[[(12-Chloro-5-naphthacenyl)methyl]amino]-2-methyl-1,3-propanediol hydrochloride Using the reductive amination procedure outlined in Example 1 except that the crude free base was dissolved in ethanolic HCl, 12-chloronaphthacene-5-carbaldehyde (6A) and 2-amino-2-methyl-1,3-propanediol (Aldrich) gave a 38.6% yield of 2-[[(12-chloro-5-naphthacenyl)methyl]amino]-2-methyl-1,3-propanediol hydrochloride, mp >300°, (CH₃OH/Et₂O), (C, H, N, Cl).

Example 7.
2-[(Benz[a]anthracen-3-ylmethyl)amino]-2-methyl-1,3-propanediol 7A.
5,6,8,9,10,11-Hexahydrobenz[a]anthracene-3-carbaldehyde 5,6,8,9,10,11-Hexahydrobenz[a]anthracene (Cambridge Chemicals, Inc. 38.0 g, 0.162 mol) was formylated using the procedure of A. Rieche et al., (*Chem. Ber.* 93, 88 (1960)). The crude aldehyde mixture was passed through a 40×10 cm plug of SiO₂ using PhCH₃ as the eluting solvent. Three aldehyde fractions were isolated. The least mobile of the fractions by TLC contained 11.23 g (26.5% yield) of crude 5,6,8,9,10,11-hexahydrobenz[a]anthracene-3-carbaldehyde (identified by ¹H-NMR) which was used directly without further purification.

7B. Benz[a]anthracene-3-carbaldehyde

To a RB flask equipped with magnetic stirring bar, reflux condenser and N₂ inlet line with bubbler added 5,6,8,9,10,11-hexahydrobenz[a]anthracene-3-carbaldehyde (7A, 10.41 g, 39.7 mmol), 2,3-dichloro-5,6-dicyano-1,4-benzoquinone (DDQ) (Aldrich, 27.02 g, 0.119 mol) and dry PhCH₃ (500 mL). The mixture was refluxed for 2 h until no more starting material remained by TLC, cooled and filtered to give a deep red solution. The solution was applied to a 40×10 cm column of SiO₂ and eluted with additional PhCH₃ as the solvent. The appropriate fractions were combined with the solvent removed to give 6.01 g of crude material. This was crystallized twice from PhCH₃/hexane (1:4) and dried to give 2.94 g (28.9% yield) of benz[a]anthracene-3-carbaldehyde, mp 144°–145°, (C, H).

7C.
2-([Benz[a]anthracen-3-ylmethyl)amino]-2-methyl-1,3-propanediol methanesulfonate Using the reductive amination procedure outlined in Example 1, benz[a]anthracene-3-carbaldehyde (7B) and 2-amino-2-methyl-1,3-propanediol (Aldrich) gave a 52.7% yield of 2-[(benz[a]anthracen-3-ylmethyl)amino]-2-methyl-1,3-propanediol methanesulfonate, mp 189°–191.5°, (C, H, N, S) (i-PrOH/Et₂O).

Example 8.
2-[(4H-Cyclopenta[def]phenanthren-1-ylmethyl)amino]-2-methyl-1,3-propanediol 8A. 4H-Cyclopenta[def]phenanthrene-1-carbaldehyde 4H-Cyclopenta[def]phenanthrene (Aldrich) was formylated using the procedure of A. Rieche et al., (*Chem. Ber.* 93, 88 (1960)). The crude aldehyde was passed through a plug of silica gel using CH₂Cl₂ as the eluting solvent. The appropriate fractions were combined and the solvent removed to give 48 g of product. This was recrystallized from hexane to give 28.1 g (53.6% yield) of pure 4H-cyclopenta[def]phenanthrene-1-carbaldehyde, mp 209°–212°, (C, H).

8B.
2-[(4H-Cyclopenta[def]phenanthren-1-ylmethyl)amino]-2-methyl-1,3-propanediol methanesulfonate.0.05 i-PrOH Using the reductive amination procedure outlined in Example 1, 4H-cyclopenta[def]phenanthrene-1-carbaldehyde (8A) and 2-amino-2-methyl-1,3-propanediol (Aldrich) gave a 10% yield of 2-[(4H-cyclopenta[def]phenanthren-1-ylmethyl)amino]-2-methyl-1,3-propanediol methanesulfonate 0.05 i-PrOH, mp 160°–162°, (C, H, N, S) (EtOH/Et₂O).

Example 9.
2-[[(4,5-Dihydro-6-acephenanthrylenyl)methyl]amino]-2-methyl-1,3-propanediol methanesulfonate Using the reductive amination procedure outlined in Example 1, 4,5-dihydro-6-acephenanthrylenecarbaldehyde (J. P. Hoeffinger, P. Jacquignon, and N. P. Buu-Hoi, *Bull. Soc. Chim. Fr.* 974 (1970)) and 2-amino-2-methyl-1,3-propanediol (Aldrich) gave 74% yield of 2-[[(4,5-dihydro-6-acephenanthrylenyl)methyl]amino]-2-methyl-1,3-propanediol methanesulfonate, mp 240°–242° (dec), (C, H, N, S) (EtOH/hexane).

Example 10.
2-[(6-Acephenanthrylenylmethyl)amino]-2-methyl-1,3-propanediol

10A. Acephenanthrylene-6-carbaldehyde

Using the dehydrogenation procedure outlined in Example 7B, 4,5-dihydroacephenanthrylene-6-carbaldehyde (J. P. Hoeffinger, P. Jacquignon, and N. P. Buu-Hoi, *Bull. Soc. Chim. Fr.* 974 (1970)) gave a 35.8% yield of 6-acephenanthrylenecarbaldehyde, mp 161°–163° (dec), (C, H), (PhCH₃/hexane).

10B.
2-[(6-Acephenanthrylenylmethyl)amino]-2-methyl-1,3-propanediol methanesulfonate Using the reductive amination procedure outlined in Example 1, acephenanthrylene-6-carbaldehyde (10A) and 2-amino-2-methyl-1,3-propanediol (Aldrich) gave a 61.5% yield of 2-[(6-acephenanthrylenylmethyl)amino]-

2-methyl-1,3-propanediol methanesulfonate, mp 232°–233° (dec), (C, H, N, S) (EtOH/Et$_2$O).

Antitumor Screening Results

Methods for evaluating the antitumor activity of these compounds are essentially those used in the Tumor Panel by the Developmental Therapeutics Program, Division of Cancer Treatment, National Cancer Institute, A. Goldin, et al., *Methods in Cancer Research*, Vol. XVI, p. 165, Academic Press (1979). Some modifications, in dose level and schedule have been made to increase the testing efficiency.

Example 11. Lymphocytic Leukemia P388/0 Test

CD2-F$_1$ mice, of the same sex, weighing 20±3 g, are used for this test. Control and test animals are injected intraperitoneally with a suspension of ~10$^6$ viable P388/0 tumor cells on day 0. In each test, several dose levels which bracket the LD$_{20}$ of the compound are evaluated; each dose level group contains six animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animals' body weights. The day of death for each animal is recorded, the median identified for each group and the ratios of median survival time for treated (T)/control (C) groups are calculated. The criterion for activity is T/C×100≦120%. Results of P338/0 testing are summarized in Table I below.

TABLE I

| Compound of Formula | Optimal Dose (mg/kg) | T/C × 100% (Excluding 30 Day Survivors) | 30 Day Survivors | LD$_{20}$ (mg/kg) |
|---|---|---|---|---|
| 1 | 220 | +270 | 2/6 | 180 |
| 2 | 111 | +204 | 0/6 | 100 |
| 3C | 50 | +250 | 0/6 | 40 |
| 4B | 225 | +280 | 2/5 | 250 |
| 5B | 15 | +140 | 0/6 | 7.5 |
| 6B | 75 | +150 | 0/6 | 70 |
| 6C | 45 | +150 | 0/6 | 67.5 |
| 7C | 200 | +120 | 0/6 | 200 |
| 8B | 30 | +145 | 0/6 | 225 |
| 9 | 60 | +215 | 2/6 | 50 |
| 10 | 110 | +270 | 2/6 | 100 |

Example 12. Formulation Examples

A. TABLET

| Compound of Formula I | 500.0 mg |
|---|---|
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

B. TABLET

| Compound of formula (I) | 500.0 mg |
|---|---|
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corn starch and lactose. The powders are wetted with a solution of polyvinylpyrrolidone dissolved in a mixture of purified water and denatured alcohol to form granules. The granules are dried and mixed with the powdered stearic acid and magnesium stearate. The formulation is then compressed into tablets weighing approximately 700 mg each.

C. CAPSULES

| Compound of formula (I) | 500.0 mg |
|---|---|
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

D. SYRUP

| Compound of formula (I) | 250.0 mg |
|---|---|
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water | q.s. to 5.0 mL |

The compound of formula (I) is dissolved in the ethanol, glycerin, and a portion of the purified water. The sucrose and preserving agent are dissolved in another portion of hot purified water, and then the colouring agent is added and dissolved. The two solutions are mixed and cooled before the flavoring agent is added. Purified water is added to final volume. The resulting syrup is thoroughly mixed.

E. IV INJECTION

| Compound of formula (I) | 5.0 mg |
|---|---|
| Glycerin | q.s. for isotonicity |
| Preservative | 0.1% |
| Hydrochloric Acid or | as needed for |
| Sodium Hydroxide | pH adjustment |
| Water for Injection | q.s. to 1 mL |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 mL ampules or vials.

What is claimed is:

1. A compound of the formula

or a pharmaceutically acceptable acid addition salt thereof wherein $R^1$ contains not more than eight carbon atoms and is a group

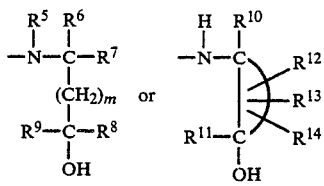

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl and Ar is 4,5-dihydroacephenanthrene.

2. The compound or salt of claim 1 in which $R^1$ is

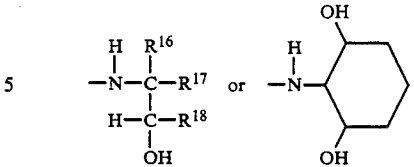

wherein
m is 0; $R^{16}$ is $CH_2OH$, $CH(CH_3)OH$ or $CH_2CH_2OH$;
$R^{17}$ is hydrogen, $C_{1-3}$ alkyl or $CH_2OH$; and
$R^{18}$ is hydrogen or methyl.

3. A compound or salt of claim 2 wherein $R^{16}$ is $CH_2OH$ or $CH(CH_3)OH$ and $R^{17}$ is hydrogen, methyl, ethyl or $CH_2OH$.

4. A compound or salt of claim 1 wherein $R^1$ is a diol of the structure

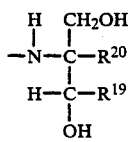

wherein $R^{19}$ is hydrogen or methyl and $R^{20}$ is hydrogen, methyl or ethyl.

5. A compound or salt of claim 4 wherein $R^{20}$ is methyl.

6. A compound or salt of claim 5 in which $R^{19}$ is hydrogen.

7. A compound or salt of claim 5 in which $R^{19}$ is methyl.

* * * * *